United States Patent
Chawla (10) Patent No.: US 7,116,798 B1
(45) Date of Patent: Oct. 3, 2006

(54) FARE CARD EXPLOSIVE DETECTION SYSTEM AND PROCESS

(76) Inventor: Manmohan Singh Chawla, 3300 Rosemary La., University Park, MD (US) 20782

(*) Notice: Subject to any disclaimer, the term of this patent is extended or adjusted under 35 U.S.C. 154(b) by 0 days.

(21) Appl. No.: 11/176,346

(22) Filed: Jul. 8, 2005

(51) Int. Cl.
G06K 9/00 (2006.01)

(52) U.S. Cl. .................................................... 382/100
(58) Field of Classification Search ............... 382/100; 356/311–318; 250/339.11, 339.12, 341.1–341.8, 250/281, 282; 378/57, 62
See application file for complete search history.

(56) References Cited

U.S. PATENT DOCUMENTS

| | | | |
|---|---|---|---|
| 5,364,795 A | 11/1994 | Sausa et al. | |
| 5,638,166 A | 6/1997 | Funsten et al. | |
| 5,760,898 A | 6/1998 | Haley et al. | |
| 5,818,047 A | 10/1998 | Chaney et al. | |
| 5,912,466 A | 6/1999 | Funsten et al. | |
| 6,610,977 B1 | 8/2003 | Megerle | |
| 6,797,944 B1 | 9/2004 | Nguyen et al. | |
| 2004/0051867 A1 | 3/2004 | Brestel et al. | |
| 2004/0124376 A1 | 7/2004 | Valentinovich et al. | |

FOREIGN PATENT DOCUMENTS

EP 455516 A2 11/1991

OTHER PUBLICATIONS

Sepaniak Michael et al., "Microcantilever Transducers: A New Approach in Sensor Technology," Analytical Chemistry, Nov. 1, 2002, pp. 568-575A, vol. 72, Amer. Chem. Society, USA.
Pinnaduwage et al., "Sensitive Detection of Plastic Explosives . . . Monolayer-coated Microcantilevers," Applied Physics Ltrs, Aug. 18, 2003, pp. 1471-1473, vol. 83, No. 7, AIP, USA.

Primary Examiner—Samir Ahmed
Assistant Examiner—Craig W. Kronenthal
(74) Attorney, Agent, or Firm—Donald Grant Kelly (57) ABSTRACT

A substrate card, in the form of a Metrocard®, farecard, keycard, passport, boarding pass or the like, presented for controlled gateway passage at an automatic reader, is photographed and the captured card image is digitized. The card then is heated to a point where trace explosive present on the card is subjected to an energetic reaction imparting a char smudge signature. The card is cooled and a second image is captured and digitized. The digitized images are subjected to a subtractor stage resulting in an isolated char smudge signature image possibly in the form of at least a partial fingerprint residue recognizable by a computer. Upon char image detection, which may include a fingerprint matching process, the computer directs the controlled gateway to restrain the card presenter and secure the card as evidence. The card may be pre-coated to avoid ignition and to enhance trace material adhesion.

21 Claims, 4 Drawing Sheets

FARE CARD EXPLOSIVE DETECTION SYSTEM AND PROCESS

REFERENCE TO RELATED APPLICATIONS

Not applicable

STATEMENT REGARDING FEDERALLY SPONSORED RESEARCH OR DEVELOPMENT

Not applicable

REFERENCE TO SEQUENCE LISTING

Not applicable

BACKGROUND OF INVENTION

1. Field of the Invention

This invention relates to the field of explosive detection, particularly in the area of trace detection and forensic evidence collection.

2. Description of Related Art

Explosives are essential components of conventional, chemical, biological and nuclear weapons as well as improvised terrorist devices such as car bombs, letter bombs, luggage bombs and personal or suicide bombs.

There are several methods and devices currently operating to detect explosives, and each has its own special application and optimum operating environment. Generally speaking, there are two principal categories of explosive detection techniques: bulk detection and trace detection.

Bulk detection is usually macroscopic in nature, and often carried out by viewing images provided by x-ray radiographic equipment or related imaging technology such as computed tomography (CT).

Another popular method of identifying articles and/or individuals associated with explosives includes the use of canines. The deployment of dogs to discover or track explosives has its advantages and disadvantages. On the negative side, persons subjected to canine inspection may feel threatened or offended. Besides, the liability attached to such inspections is obvious. Moreover, dogs have duty cycle limits, in that they are limited to but one hour of work without a break. Perhaps the most significant limitation to their usefulness is their inability to communicate to the handler the type of explosive detected.

On the positive side, dogs can be conditioned to track and identify almost any substance that is volatile, and with impressive accuracy. More importantly, dogs have at least the capacity, though limited, to make a physical connection between a detected substance and its associated human source. More recently, honeybees are being preconditioned to make targeted discoveries during their wide-ranging foraging efforts. University of Wyoming researchers in this area train bees to find such targets as explosive material and drugs.

Another method of testing for the presence of explosives involves bulk detection by x-ray imaging of a container or package so as to discover metal parts used in fuzes and/or wiring required for proper functioning. Still another method involves neutron activation of the chemical elements such as carbon, oxygen and nitrogen that make up the explosives.

Regardless of method or device, responsive and reliable explosive detection development remains a priority in the present climate of global terrorism. For a number of reasons, significant research and developmental resources are shifting to trace evidence tracking and discovery. This is particularly the case since interpretation of X-ray or CT images is highly labor intensive and subjective. The result of this shift is the emergence of varied embodiments of trace detectors that are highly effective in discovering minute amounts of explosive.

Typical of such trace detection techniques are systems involving Ion Mobility Spectrometry (IMS), Chemiluminescence, Electron Capture Detectors (ECD), Surface Acoustic Wave Sensors (SAW), or system combinations such as ECD and Chemiluminescence detectors, or SAW and front-end Gas Chromatograph (GC).

Then, too, there are the Thermo-Redox detectors and a technique called Field Ion Spectrometry. Perhaps more well known are the highly developed Mass Spectrometry systems, and the recently developed EXPRAY field test kit. Still other relatively newer techniques or devices for trace detection have emerged in the form of the Thermal Neutron Activation (TNA) system, the 14.7 MeV neutron interrogation system, and the Pulsed Fast Neutron Analysis (PFNA) technique currently under development by SAIC, Inc.

More techniques under recent development include the Quadrupole Resonance (QR) technique (developed by Quantum Magnetic Inc.), and the Portable Isotopic Neutron Spectroscopy (PINS) chemical assay system developed jointly by EG&G Ortec, Inc. along with the Idaho National Engineering and Environmental Laboratory.

Current methods for detecting explosives on humans, particularly when they are entering portals to transportation systems or important facilities, include the removal of particulates by air blasts directed toward possibly contaminated areas such as hands, pockets, belt area and handbags, and subsequently capturing the residue.

The air blast and particulate capture in such systems are followed by pre-concentrating and heating the residue and detecting the unwelcome substance by employing one or more of the many sensitive techniques such as Ion Mobility Spectrometry (IMS), Gas Chromatography (GS), Mass Spectrometry (MS) and other such processes.

These systems and methods are typical of those commonly used when inspecting people and/or their baggage or other personal items. For example, passengers entering air or ground transit, as well as attendees at a massive ticketed event, find themselves subjected to this type of inspection. However, such systems and methods are only as effective as the time or opportunity allowed for such inspection. At best, such inspections can be intrusive; at worst, even abusive.

Obviously, in the interest of time, efficiency, and human comfort, everyone in a card/pass holder queue cannot be tested by these complex systems. Currently, inspections must be limited to subjects randomly selected (or pre-identified by some form of prescreening technique) so as to avoid disturbing and/or delaying the entire card/pass holding queue. Besides the issue of time, there are further issues of logistics, physical layout for the equipment, trained supervised staffing and so forth.

Under constraints of time and space, and the ever-present need to avoid obstructing passenger or patron traffic, the tasks of capturing and evaluating trace evidence are vexing. The challenge becomes insurmountable with the growth of demand for reliance on such inspections and with the constant expansion of facilities that require such safeguards. Hence, these trace evidence discovery systems are becoming ubiquitous.

According to the National Institute of Standards and Technology (NIST), around 20,000 IMS units currently are deployed worldwide, with more than 7000 of those placed at US airports. Vast numbers of units are in place at embassies, stadiums, courthouses, and so on. The demand for enhanced security at every turn is exploding. With this explosion, there is a growing need to strengthen metrology and develop reliable standards to support ever-widening deployment. Even as trace detection quality is refined, the overall methodology currently in place is flawed for a number of reasons.

Current trace detection processes, regardless of the substance residue testing method, usually require detention or retention of persons, luggage, and so forth identified through earlier screening processes as persons or items of interest. Pre-screening, as by profiling or behavioral observation, obviously has its limitations. Current trace discovery technology also has its limiting issues. Such techniques are not always successful due to the lack of sufficient quantity of traces, insufficient time for thorough analysis, or simply because the traces are never easily identified.

Many explosives have a very low vapor pressure making detection particularly challenging to existing technologies. An example of such an explosive is SEMTEX, a plastic explosive manufactured in the Czech Republic. SEMTEX is difficult to trace since it has no detectable smell, and has been used by extremist groups in the Middle East, Libya, Balkans and by the IRA in Northern Ireland.

Other low vapor pressure explosives particularly challenging to existing trace discovery technology are pentaerythritol tetranitrate (PETN) and hexahydro-trinitro triazine (RDX), both commonly employed in terrorist bombings. These can easily be molded for concealment. Only relatively small amounts of these substances can bring down large aircraft, destroy buildings and wreak havoc on rail transit systems.

Examples of techniques and apparatus for detecting the presence of trace evidence of explosive abound. With respect to the present invention, the more pertinent documents uncovered in patent literature searches are embodied in the following patent documents.

Haley et al., in U.S. Pat. No. 5,760,898, disclose a technique for detecting traces of explosive material, for example on a suitcase, by applying laser radiation to the surface thereof. This causes micro-detonation of any trace particles thus enabling detection of the explosive by its characteristic emission.

In U.S. Pat. Nos. 5,638,166 and 5,912,466 issued to Funsten et al., a photomultiplier, a charge couple device or a photodiode is used to detect ultraviolet emissions resulting from heating of explosive purportedly resulting in deflagration. An apparatus and method presented by Sousa et al. in their U.S. Pat. No. 5,364,795 may be employed to detect the presence or absence of propellants, explosives, and nitro pollutants, wherein a laser photon fragments a target molecule and facilitates detection of the characteristic NO fragment.

Laser energy is also key to the detection system of Brestel et al. disclosed in Published US Patent Application No. 2004/0051867, wherein at least one laser illuminates a portion of an object and either a second harmonic detector or a luminescence controlled substance detector, or both are used. Additionally, the Brestel et al. system includes a Raman scattering based substance detector.

Megerle's U.S. Pat. No. 6,610,977 discloses a method and apparatus for screening an object for the presence of an explosive, chemical warfare agent, biological warfare agent, drug, metal, weapon, and/or radioactive material. The apparatus includes a portal through which the object is arranged to pass, the portal including a housing equipped with an ion mobility spectrometer and a surface acoustic wave device for detecting explosives, drugs and chemical warfare agents. In another embodiment the housing is equipped with a biological warfare agent detector, chemical warfare agent detector, metal detector, x-ray system, and/or radiation detector.

Nguyen et al., in U.S. Pat. No. 6,797,944, disclose a laser desorption and detection of explosives, narcotics and other chemical substances. The Nguyen et al. technique employs a compact scanning apparatus including an optical system to deliver a beam of pulsed infrared laser light that illuminates an interrogation area of the surface.

The illumination described by Nguyen et al. is sufficiently intense and of such duration as to cause selective ablation of molecules of contraband substance present on a surface without substantially damaging the surface. A portion or sampling of the ablated molecules is collected and transferred to a separate chemical analysis system where a detector reacts to the sampled portion and activates an audible or visible alarm. A traceable residue of the detected contraband is left on the article for subsequent forensic analysis.

In EPO455516, Akery et al. present a security system for an airport or the like where an item such as a ticket or a boarding card is checked to see if it holds traces of explosive or other contraband picked up from the passenger's hands. According to the invention, a prospective passenger is handed a boarding card, landing card, identity card or like item for use in gaining passage beyond a check point. The card or like item is such as to absorb traces of explosives and other contraband material from the passenger's hands should such traces be present thereon.

After the card has been handled by the passenger, Akery et al. explain that at least part of the card is tested for the presence of any of said traces. Before boarding the aircraft, passengers are required to insert their cards into a card analyzer. This analyzer consists of apparatus for determining the presence of trace levels of single or multiple explosive types from the surface of the card.

The analysis in the Akery et al. patent may include heating the surface of the card and passing the desorbed particles into a Grace Gas Analyzer. Alternatively, the analysis may employ a liquid or gaseous solvent to remove the absorbed materials from the surface preceding trace chemical analysis. The chemical analysis may include mass spectrometry, gas chromomatography, ion mobility spectrometry, etc.

The magnetic strip on a card also is read in a reader/analyzer and the information thereon passed to the airline's computer system, as further disclosed by the Akery et al. patent. The presence of explosives and the card holder's identity are indicated on a monitor to security staff who can take appropriate action.

In U.S. Pat. No. 5,818,047, Chaney et al. also address airport security. The Chaney et al. patent disclosure focuses in particular on SEMTEX plastic explosive in a sample such as a fingerprint. The explosive trace is detected by Raman spectroscopy as a boarding card is fed into a boarding card reader for otherwise normal processing prior to boarding.

The Chaney et al. patent explains that as the boarding card is transported by the boarding card reader, it is scanned by a laser, for example, a gas laser such the Helium-Neon type. A dichroic filter reflects the laser light and focuses it on the card. Filtered Raman scattered light is collected and focused by a lens onto a detector, such as an avalanche photodiode. This detector reacts to indication of the presence of explosive trace.

One particular advantage of the Raman analysis technique employed by Chaney et al. is that it is non-destructive.

Hence, if SEMTEX explosive substance is detected, the card can be retained for further analysis and for use as evidence. Such systems can be modified for detecting SEMTEX explosive material on other surfaces such as tickets, identity cards, passports, and so forth. Further, according to Chaney et al., such systems may be used in situations other than an airport boarding card reader, e.g. at the entrances to public buildings, government offices and the like. The non-destructive nature of the Raman analysis lends itself to such situations, since the ticket, card and such can be handed back to the holder after analysis.

To enhance the performance of the Chaney et al. system, the patent disclosure suggests coating the card with a thin layer of a material such as silver, gold or copper, and providing it with a suitably roughened surface such that molecules of substances such as RDX or PETN will be adsorbed onto the roughened surface and would thus exhibit surface enhanced Raman scattering.

Valentinovich et al., in Published US Patent Application 2004/0124376, disclose a system and an apparatus for detecting explosive in real time. The apparatus involves a chamber in which items pass through or people walk through for detecting said explosive particles in real time. The explosive particles from either the people or items will be deposited into a cell by an influx of air flow from the chamber to the cell.

The cell described by Valentinovich et al. includes a heating device and an optical scheme. The cell is heated to a predetermined temperature in which the explosive particles are divided into small molecular components that can be detected. The optical scheme detects the smaller molecules. The computer system controls the apparatus and analyzes the data gathered.

These old and more recently developed systems and techniques, as just described, have unique strengths and shortcomings. The latter reflect a lack of adaptability to field application, particularly with respect to challenges presented by fast-moving masses of people passing checkpoints or dealing with automated ticket collectors for transit systems and major events across the country and across the planet.

Attempts to apply existing technologies in solving the myriad of issues in this field result in the construction of highly complex and relatively expensive systems. They demand well-trained, highly skilled and experienced personnel and require constant, personal monitoring and participation. Too often, subjective judgment must be relied upon. And, importantly, few if any of these systems (other than the trusty canine) can establish a direct link between discovered trace evidence and the human perpetrator.

The invention presented herein as the subject of this application addresses the above noted problems and shortcomings in a unique manner, while drawing upon off-the-shelf detection and analysis technologies assembled and applied in a new and unobvious manner and achieving wholly unexpected results. To achieve this, the present invention takes advantage of some basic principles observed with respect to explosive trace evidence, but not heretofore exploited in the trace detection field.

As demonstrated by the prior art discussed hereabove, it is well known that surfaces brought into contact with commercial, military or improvised explosives become contaminated with traces of explosive particulates. Such surfaces may include, but are not limited to, luggage coverings, purse fabric, and bare skin, as well as tickets, boarding passes, electronic key cards, passports and the like which typically are presented for facility entry, passage to major events, or boarding transit conveyances or systems.

Trace evidence contamination may have its origins during explosive manufacturing, packaging or subsequent handling stages of such explosives. Also, the explosive-related contaminants are well known to be sticky in nature, thus having a tendency to linger on the handlers' hands, particularly within skin patterns such as typical fingertip whorls, loops or arches. The stubborn, sticky contaminants often will remain on the hands and other surfaces of interest for several hours despite repeated washing.

The proposed technique employed with respect to the present invention includes direct observance of yet another property common to explosives. Upon detonation, all explosives undergo an exothermic reaction resulting in the generation of significant heat. In minute traces, explosion is not likely since the dimension of explosive particulate is less than a diameter critical to sustained detonation. However, explosive material in very small sizes or traces will, when subjected to a rapid heating process, deliver a relatively large amount of heat whether it detonates or deflagrates. Sufficient heating is certain to bring about an energetic, if not sustained, reaction.

In the present invention, one of the techniques to initiate or activate an explosive trace involves heating a trace evidence on a substrate to a temperature higher than the critical temperature where an exothermic reaction would set in, but not so high that the substrate is destroyed. The intent herein is to employ heat in driving the explosive substance to react in such a way that the resultant reaction delivers an identifiable signature to the substrate, as will be explained.

As inferred hereabove, the fingers or other portions of the hands of a person working with explosives typically will carry or retain at least a few micrograms of explosive residue. Despite all determined efforts to avoid it, fingerprints of explosive handlers invariably will be transferred to any surfaces or items touched or handled, as for example boarding passes, tickets, coupon, transit transfers, key cards, currency, fare cards and the like.

As an example, it has been recognized that fare cards employed to access mass transit trains such as London's Tube, the Metro transit lines running in Washington, D.C., or the Subway system in New York City and similar mass transit systems in other metropolitan areas can be found to carry trace evidence of explosive residue. Boarding passes (generally in the form of cards) for gaining access to aircraft or long distance passenger trains could also carry similar residue-contaminated fingerprints. Finger prints, however, generally are invisible to the unaided eye, even if they contain explosive trace evidence. While latent fingerprints may be revealed or made more visible through application of vapors of iodine or by Superglue®, neither application will be successful in detecting explosive traces.

Testing for explosive traces on boarding passes and fare cards has been postulated in the past; however, the question remains: How best to deal with such trace evidence in an effective and efficient manner, and in a way that is essentially nondestructive such that forensic evidence is retained. Further questions: a. how best to do this in real time and automatically, and in such as way as to avoid traffic disruption or excessive invasiveness; b. how best to test for explosive traces and unequivocally tie such traces to a perpertrator?

Fare computations, e.g., date/time, points of embarkation and destination, and other data, presently are routinely read by well-known automatic scanners at subway turnstiles and airline boarding gateways. In some instances as discussed above, trace explosive evidence on boarding passes purportedly has been detected by sophisticated scanning devices such as the Raman Spectroscopy or ablation by lasers and the characteristics of the ignition evaluated. However, while such data are read by scanners, no method currently exists to actually capture or reveal fingerprints directly associated with or related to such evidence.

Thus, while fingerprints (and/or prints of other portions of the hand) contaminated by explosive trace evidence most likely appear on fare cards and boarding passes, processes for capturing the trace in situ and reading or capturing the prints did not exist prior to the present invention. Further, until the present invention, there was no known technique or system by which trace evidence could be analyzed in real time and without significant passenger traffic disruption (e.g., during a normal scan/read operation of a transit fare card and the like) and in such a way as not to result in bottlenecks at gateways or turnstiles.

Department of Homeland Security (DHS) experts naturally have identified such gateways as crucial to protection of a threatened public. Up to this point in time, general thinking has dictated that, even if trace evidence could be captured and evaluated, such a complex process would be far from convenient or economically feasible, and thus would be rejected as raising unacceptable barriers and cost margins for the traveling public.

Until now, and without extensive, laborious and individually-targeted screening techniques, singling-out individuals as they are queued for passing portals and perhaps carrying trace evidence of explosive handling has been impractical and far from cost effective. There is a long felt need for an automated system and process for examining substrates, articles or material touched and handled by individuals, and capturing evidence instantly linked to a bearer who also handled explosive materials. This also must be a real-time technique applied as subjects are constrained to pass, one by one, through a validation checkpoint (e.g., airport gateway, transit turnstile, entrances to pavilions, concert halls, civic centers and the like).

The requisite presentation of Metrocards®, fare cards, boarding passes, tickets, passports and the like by people queued at a checkpoint, turnstile or gateway for travel or events offers distinct opportunities for gathering trace evidence, since such cards, passes and the like must be physically handled by their bearers or presenters.

The present inventive system and process effectively resolves the shortcomings and inadequacies of the prior art in satisfying the long felt need.

BRIEF SUMMARY OF THE INVENTION

The principal objective of the invention described below is to provide a unique system and method for detecting trace evidence of an explosive in, or on, fingerprints or handprints captured from Metrocards®, fare cards, boarding passes, passports and the like (subsequently referred to simply as card or cards), and to utilize such trace evidence to earmark the card as irrefutable evidence of a traveler's prior or current association with an explosive tainted card. Further, it is an objective of the present invention to positively link said evidence to a specific suspect or explosive material handler.

Beyond that, another objective is to present a system and method that will enable sensing said explosive trace evidence, capturing images of the associated (smudged, charred, contaminated or dirty) fingerprints or handprints resulting from the explosive trace, and signaling an operator or secondary system elements to control further movements of a discovered suspect.

Finally, it is a still further objective that the unique system and method provide such scanning, detection and control in an effective and efficient manner while passage is not unduly disrupted and the passengers or patrons whose items are subject to scan are not themselves violated or threatened.

The proposed explosive detection system uses commercially available technologies that can be incorporated, for example, in turnstile fare card readers, in boarding pass readers of airline gateways, portals of pavilions and stadiums, and similar check points. In fact the proposed system and method will find ready application wherever efforts are undertaken to detect and identify explosive trace evidence on any substrate.

While not intended as claim scope-limiting environments, the inventive system and process are described below in the context of a fare card or Metrocard® turnstile reader.

Typically, a fare card including a substrate or medium on which is encoded data relative to its purpose is inserted into an automatic reader. The card may be drawn into the reader in a manner well known in the art, e.g., by high speed mechanical rollers or pneumatic conveyors. In addition to the normally required processing of such cards, a number of inspection actions take place in rapid progression.

At a certain position along the automatic reader's internal path, an image capture unit, for example in the form of a digital camera or the like, may be utilized to photograph or otherwise capture an initial image of one or both sides of the card. An associated digitizer converts the captured image to a digital signal for further processing. More will be explained herebelow about this image capture and digitizer arrangement. The card is subjected in a subsequent stage to an intense heat source directing heat toward at least one side thereof.

In one embodiment, this intense heat source is embodied as at least one, or a pair of, temperature-controlled and position-controlled, rapid heating hot plates. The plate or plates may be arranged so as to apply heat to at least one side of the card, yet without significant or prolonged contact with the surface thereof so as to avoid overheating or slowing card movement. Other equivalent heat sources could be employed as will be explained.

As the card is rapidly heated, any explosive residue, even in the slightest amount, transferred thereto in a fingerprint or handprint is heated to a given temperature level. For purposes of description, this temperature level will be described as the threshold or critical temperature, and must be at least high enough to initiate an exothermic or energetic reaction in said residue while avoiding conflagration, melting or marked damage to the medium or substrate of said card.

In other words, the threshold or critical temperature in this heating stage is high enough to initiate an energetic reaction, but still avoid reaching the ignition point of the card/pass. In some instances, however, the threshold or critical temperature will be at a level where ordinary untreated paper will ignite (typically at 233 C). Hence, it may be advisable in some cases to modify the medium of the card to accommodate this detection process.

As examples: (a) fireproof substrate; (b) suppressant chemicals; and/or (3) metal-coatings can be used to delay or avoid the onset of paper ignition or plastic melting. Alternatively thin aluminum (or alternative metal) foils can be deployed as surface layers. It is important, however, that the nature of the card substrate surface be such that fingerprints may be relatively easily retained and subsequently read as will be discussed below. To this end, pre-treating the surfaces of Metrocards®, fare cards, boarding passes, passports and the like with a monolayer coating of 4-mercaptobenzoic acid (4-MBA) will enhance adsorption of any explosive material trace present.

At the high temperatures reached during the heating stage, grease fingerprints or similar hand smudges of oil or lotions, food substances, perspiration and the like will be vaporized. However, black smudge marks resulting from an energetic reaction of any explosive trace particles or molecules will remain. Such char or smudge mark traces can, if necessary, be removed or transferred by routine image processing or transfer techniques well known in the criminal forensics field.

Alternatively, when found to be suspiciously contaminated, the card can be seized, confiscated or otherwise withdrawn from the reader path and retained as evidence. Moreover, carefully controlled heat application and measurement will further help to identify specific trace compounds. Threshold temperatures where different explosive materials achieve an energetic reaction under intense heat will vary as much as 100C. So, this invention not only detects the presence of trace evidence, it distinguishes among various compounds.

Close proximity of the card with single or dual hot ironing plates will ensure an energetic reaction of explosive traces rather than just burn. The mass of the explosive residue, at only a microgram or so, will be inconsequential in its destructive power except for charring the card so as to present images of skin ridges (as in whorls, loops or arches) of a trace contaminated fingerprint, or other identifying characteristics of a contaminated handprint.

Subsequent to the heat treatment just described, a chilling cycle or cooling stage follows to further ensure against paper ignition (or meltdown as may be the case). This chilling cycle need not be particularly cold, but should provide a relative cooling effect to avoid substrate ignition and to return the substrate to its pre-heated color. Following the chilling cycle or cooling stage, secondary card images are captured.

This secondary image capture stage serves to capture a second (post-heating) image of a card surface that may include charred signature evidence of explosive trace ignition. The associated digitizer converts the image to a digitized signal for further processing. The digitized signals from the initial image capturing stage and the second image capturing stage are fed to a subtractor stage. In the subtractor stage, performed for example by a software driven program, the difference in the pre-heated and post-heated card is determined (by subtracting the digitized initial image from the digitized second image), which difference will represent said charred signature evidence.

As illustrated, a pair of image capture units could be positioned along in serial arrangement along a pathway to capture "before" and "after" images of the card. On the other hand, to disallow or discount any differences in camera optics, temperature, ambient atmosphere or variants that might produce faulty readings, a single image capture unit can be employed. Also, when Metrocards®, fare cards, tickets, passes, passports and the like are standardized in shape and visual detail, only the "after" image might be adequate for comparison with a pre-stored, standard image.

Alternatively, the card initially may have its image captured at a single image capture station. Following image capture and image digitization, the card is heated to cause any present explosive trace to have in energetic reaction; then cooled and returned to the same, single image capture station for a second image capture and image digitization. In this latter embodiment, the card conveying mechanism could be provided with a looped or repeated, carousel or carousel-like path to effectively reposition the card in its exact pre-heat stage relative to the single image capture and digitization station. In this context, the term "carousel-like" is intended to include well known carousel conveyance constructs as well as similar conveyances that move an article along a pathway designed to double back, or returns said article, to a given starting point in its movement.

Thus, while single image capture station embodiments are possible and may suffice, dual image capture stations may have certain advantages since a card bearer may have purposely or accidentally imparted extraneous markings or soil on the card substrate.

Other advantageous alterations could involve the addition of auxiliary sensing equipment as detection and diagnostics aids. For example, in the present invention, detectable levels of vapors will be produced during a heating stage. A host of vapor detection methods and apparatuses can be employed to address and test such vapors. The added or auxiliary sensing equipment can enhance the probability of explosive trace detection and reduce the probability of false alarm.

For example, unlike TNT, many explosives have significantly low vapor pressure. The explosive known as SEMTEX is in this class. Even the most careful or intensive canine inspection may fail to identify SEMTEX. In the system and method described herein, vapor pressure increases as temperature of the explosive traces on the card/pass increases. Auxiliary vapor detection devices such as Ion Mobility Spectrometer (IMS) can detect pictogram ($10^{-12}$ g) of explosives.

In addition to direct observation of the charred signature evidence, a host of other technologies chosen from among those discussed above, as well as other known techniques, can be employed as ancillary or auxiliary techniques to increase detection probability and to reduce false alarm. For example, analyses could involve the measurement of the heat evolved in the energetic reaction using micro thermal analysis as proposed by the research team from AST products and the University of Massachusetts.

Still another auxiliary mechanism could involve the observation of momentum imparted using cantilevers. In *Applied Physics Letters* published Aug. 18, 2003 by the American Institute of Physics, Oak Ridge National Laboratory (ORNL) researchers Pinnaduwage et al. discuss the state of the art in explosive trace detection systems, particularly with respect to microcantilevers. Observance of characteristic photons in the ultraviolet range or determination of molecular vibrational spectrum using terahertz waves (T-waves) are also attractive technologies compatible with the present technique. Sepaniak et al. report other ORNL research findings in this area in the November 2002 issue of *Analytical Chemistry*, "Microcantilever Transducers: A new Approach in Sensor Technology."

Each of these measurements can enhance the confidence in the explosive signature detection and diagnostics. Again, these are ancillary or auxiliary systems optionally employed to raise confidence level. But, the essence of the present invention has to do with capturing trace evidence in the form of char smudges which may be identifiable as fingerprints.

Compared to previous and existing systems and techniques, this invention presents a number of unique advantages. First of all, the present invention affords direct observation of contaminated, smudged or dirty fingerprints or handprints. Detection is made possible through a charring effect of the explosive trace's own exothermic or energetic reaction.

Preservation of the evidence from an energetic reaction is assured, and positive identification or perpetrator linkage are made possible since the evidence includes not only the ignited traces but also images of at least portions of fingerprint ridges physically adhered to the card, thus revealing telltale whorls, loops and arches. The equipment components utilized in this invention are readily available and relatively inexpensive. They may easily be integrated into existing gateway and turnstile checkpoints with existing automatic card reader systems. Furthermore, operation of the entire system can be automated, resulting in avoidance of subjective judgment and affording enhanced reliability in the extensively repetitive operations.

Processing the card, where the heat energy present in any explosive trace essentially imparts or deposits at least a portion of a charred fingerprint image on the card, is quick and efficient. Each process can happen in mere seconds. Advantageously, the system can be designed such that a subsequent or next card processing operation in a queue may begin before completion of the preceding process so as to avoid checkpoint bottlenecks.

Importantly, the present invention advantageously avoids subjecting passengers and patrons to annoying air puffs or blasts applied for the purpose of collecting trace evidence. It also obviates need for sidetrack processing where trace evidence must be collected and taken aside for analysis. This inventive system and method permit detection of low volatility explosives such a SEMTEX which are difficult to detect with existing systems and techniques. The invention claimed herebelow is wholly compatible with existing auxiliary techniques or sensing equipment of the nature discussed hereabove.

Finally, this invention affords a distinct advantages heretofore enjoyed mainly by the canine corps, as discussed above. Namely, by detecting the explosive trace and inextricably tying the evidence to a fingerprint, the inventive system and method establish a physical connection between a detected substance and its associated human source or perpetrator. Moreover, something the canine corps cannot do, the inventive system and process can identify and communicate the discovered explosive to authorities and instantly control further passage of the perpetrator.

BRIEF DESCRIPTION OF THE DRAWINGS

The invention will be best understood by reference to the following detailed description of an illustrative embodiment when read in conjunction with the accompanying drawing(s), wherein.

DETAILED DESCRIPTION OF THE INVENTION

Details of the present invention are provided for purpose of illustration and disclosure, but are not intended as exhaustive or limited to the invention in the form disclosed. Many modifications and variations of the method and apparatus disclosed will be apparent to those of ordinary skill in the art.

The described embodiments are chosen and described in order to best explain the principles of the invention and its practical application to enable others of ordinary skill in the art to understand the invention for various embodiments with various modifications as are suited to the particular use contemplated.

Figure 1:
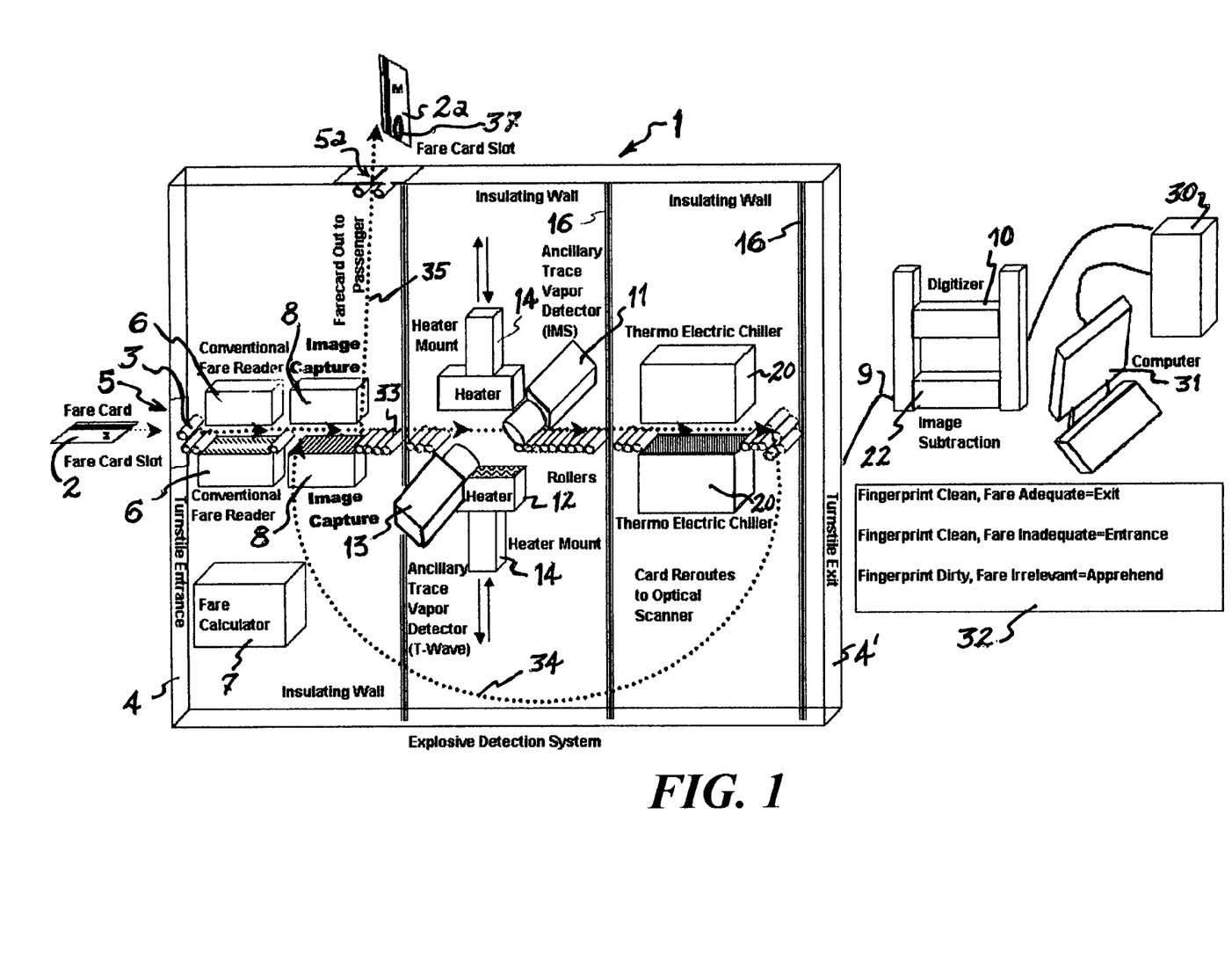
FIG. 1 is a schematic illustration of the system and method of detecting explosive trace evidence in accordance with one embodiment of the present invention.

Referring now to FIG. 1, a schematic is presented to illustrate a system 1 devised for reading a fare card 2, or the like. While described with respect to a fare card 2 presented at a controlled gateway or turnstile, it is to be understood that other cards or passes could be subjected to this same process and system. The schematic is, of course, not to scale and merely represents a system flow as card 2 is presented and processed. In the example shown this system is integrated into a checkpoint turnstile entrance 4 and exit 4', where said card 2 is fed (or drawn) through a data reader.

As viewed in FIG. 1, the card is inserted at a card intake 5 adjacent entrance 4 as the passenger (not shown) proceeds into a controlled turnstile passageway (also, not shown). Once the card 2 has completed its processing stages (to be described), the processed card 2a is retrieved by a card holder at an upper side card return 5a of said system 1. A card feeder or conveying mechanism 3 defines a relative path or pathway (33, 34, 35) of movement for said card 2 from said intake 5 to said return 5a.

A conventional card reader is illustrated as having an upper and lower reader unit; both designated for simplicity as 6. The card conveying mechanism 3 is shown herein as a roller but may also be of the typical belt or pneumatic type (or other conventional conveyance) well-known in the field of turnstile data reading systems and card transport mechanisms.

Review and interpretation of data encoded on the card occurs at a first, or reader, stage in the form of fare reader 6 which could of course be placed elsewhere along the pathway 33. Data read from the card 2 by reader 6 will be interpreted, for example by fare calculator 7 interconnected to fare reader 6. As is well known in the prior art, calculator 7 determines if the card 2 is properly presented at the present turnstile 4, and calculates whether the encoded fare is adequate or requires rejection for fare upgrade.

If this is an airline gateway passage or controlled turnstile checkpoint for a concert hall, theatre performance, meeting or other controlled attendance event, automatic reader 6 and calculator 7 would be modified or programmed to verify additional data elements such as personal identification, level of security clearance, or flight information. On a train or subway, card data would include time and destination. Of course, pertinent encoded qualifications must be present to permit the card to pass through the controlled check point. Rejection or admission will be automatic through a controlled gateway mechanism. The checkpoint includes a card 2 intake 5 and return 5a connected by pathways 33 and 35 respectively.

Once card 2 is presented to reader (or readers) 6, it moves along a pathway 33 to a first image capture stage where image capture units 8 in the form of cameras or the like capture a primary image of at least one side of card 2. While dual image capturing units 8 are shown for capturing images of both card sides, the system 1 could be limited to one.

Digitizer 10 is adapted to receive primary image via conductor 9, and to formulate a digitized primary image of said card. Primary card image data then are forwarded for further processing at an image subtractor stage 22 and computer 30 as will be described.

In a heating stage generally adjacent to the image capture stage 8, at least one side of card 2 is rapidly heated. For example, such heating may be performed by one or both of a set of opposed heater mechanisms or units 12 which can be in the form of high temperature plates constructed of metal or other material, or could be any of a variety of heating systems capable of applying or conveying high temperatures. Said heater unit 12 is adapted to heat said card 2 to a relatively high temperature such that any explosive trace substance present on said card 2 will achieve an energetic reaction imparting a char smudge to said card 2. This heating stage is explained in depth below.

Heater mechanism or unit 12 is adjustably mounted in a well known manner such as by adjustment mechanism(s) 14 so as to be selectively and carefully positioned closer to, or farther from, the card 2 in order to control heating intensity. While adjustable heating plates are featured only as an example, any of a variety of heating devices or steps can be utilized, as long as the card medium or substrate is not adversely affected. For example a laser could be used to bring the card 2 to critical temperature.

Thus, the heating stage quickly brings the surface temperature of card 2 to a predetermined critical or threshold level that results in the triggering of a thermal event, or energetic reaction, with respect to any present trace explosive. It is important to note that the present system and method will permit other cards 2 to follow in queue, as is typical of such gateway checkpoint systems.

Care is taken with temperature settings to avoid ignition or conflagration of the card 2 substrate or medium. As noted above, the card 2 medium or substrate can be specially formulated to avoid card ignition, and/or may carry a fireproof laminate or a protective coating such as metallic foil, indicated as partially applied at 2b in FIG. 2. It should be noted that while the fare card illustrated in FIG. 2 typically includes a magnetic strip (as shown) containing encoded fare and destination data, this strip is not intended as a protective coating.

Also as noted above, a monolayer coating 2c of 4-mercaptobenzoic acid (4-MBA) will enhance adsorption of any explosive material trace present. The latter coating is indicated as partially applied at 2c in FIG. 2. Of course, coatings 2b and 2c would extend entirely over both front and back surfaces of card 2.

During the heating phase, the heater mechanisms 12 will begin to impose an intensive heating effect on card 2. The heating can be enhanced either through automatically increased heat setting or automatically adjusting the proximity of heater mechanism 12 relative to the card 2, or both. As the rapid heating proceeds, an initial evaporation of various material deposits is observed. Initially evaporated substances could for example include body oils and perspiration, lotions, pollen, colognes, grease, lipstick and the like.

Shortly thereafter, any explosive trace substance present on the card undergoes an exothermic event. A microgram or so of the explosive residue will be inconsequential in its destructive power, but there will be a distinct charring of the card 2. This charring serves to deposit a signature (see FIGS. 1 and 2) on the heated card 2 surface.

Because the trace substance would have been transferred to the card by touch or grip of hand surfaces, the char signature is likely to carry unique information of significant importance in linking the card 2 to its bearer. In other words, the char deposit is likely to take the form of charred ridges with identifiable whorls, loops or arches associated with fingerprints contaminated or made dirty by the trace explosive substance.

Figure 2:
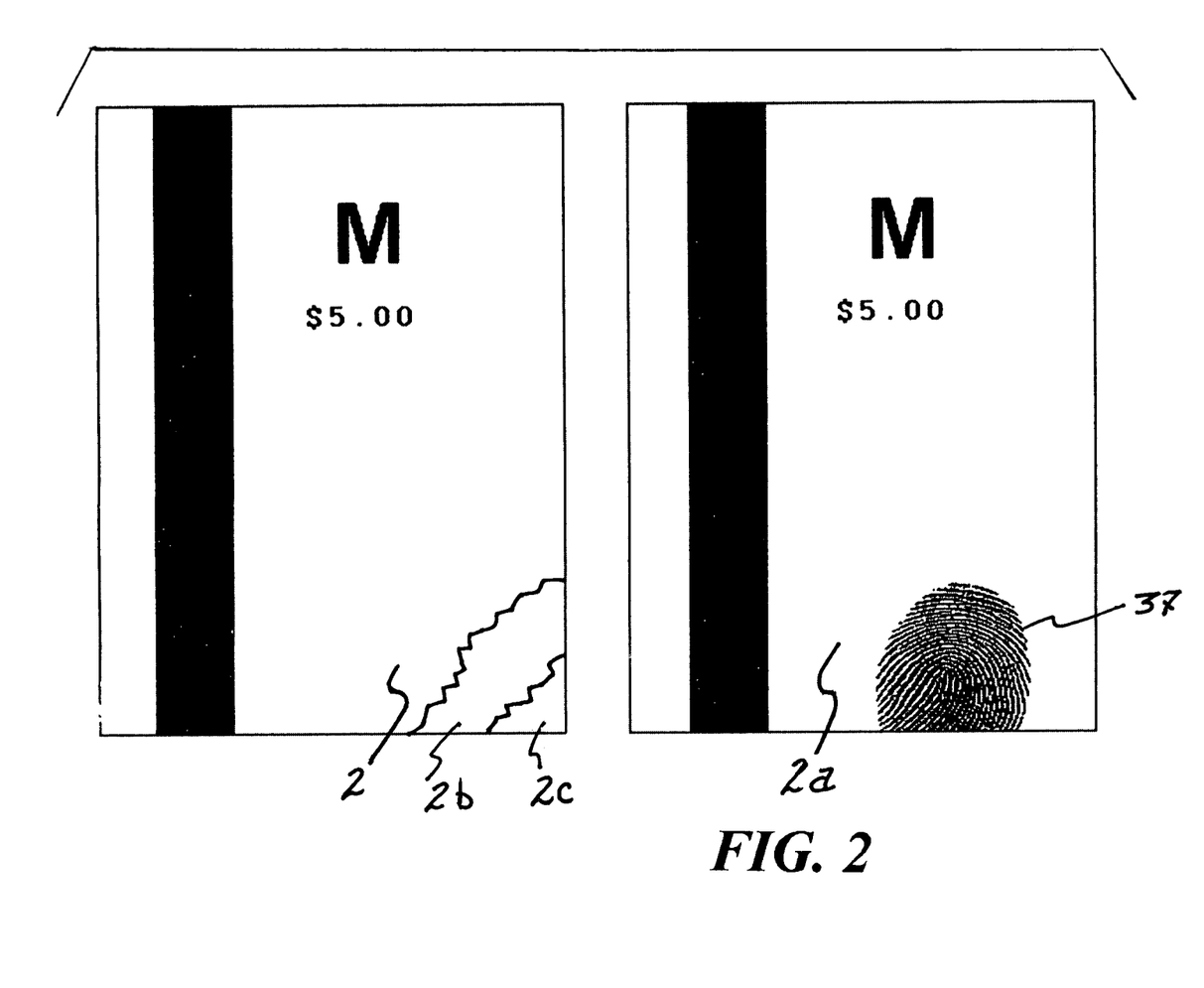
FIG. 2 represents plan views of a fare card as an example of a substrate or card that may carry trace evidence.

The minute charring, generally appears as black smudges on the card 2 as indicated, for example in FIG. 1 and FIG. 2 at 37. The char smudges are discerned or revealed electronically by employing an image subtractor stage 22 to digitally subtract a digitized card 2 image after heating from the pre-heating digitized image. This is described in more detail herebelow.

Exiting the heating phase, the heated card 2, along with its trace signature enters a rapid cooling phase. Note that the system 1 may be advantageously subdivided into chambers by including insulating walls 16, or the like. For the cooling phase, a thermoelectric chiller 20 may be employed on either side (above and/or below) of card 2. (Once again, two chillers 20 are illustrated, while one chiller 20 may suffice.) Thermoelectric chiller technology converts electrical current directly and rapidly into cooling power, without the use of cooling gasses or compressors. However, other types of chillers may be employed as is well known by the skilled artisan.

Rapid chilling of the just-heated card 2 does more than simply cool it down. The rapid cooling also has a restorative effect on the appearance of the card/pass 2. For example, bringing the card 2 to its pre-exothermic temperature serves to restore the substrate or medium color for reasons important to the subsequent stage where a second image capture will afford a comparison of preheated and post-heated images is required, as will be explained.

As card 2 exits the cooling stage (where thermoelectric chiller or chillers have cooled the card 2), said card conveying mechanism moves said card 2 relatively with respect to said heater and chiller to a second image capture stage where image capture unit(s) 8 capture a secondary image of at least said one side of card 2.

Digitizer 10 is adapted to receive said secondary image via conductor 9, and to formulate a digitized secondary image of said card 2 and said char smudge. Secondary image data are forwarded for further processing at said image subtractor stage 22. Said subtractor stage operates to electronically subtract said primary digitized image of said card 2 from said secondary digitized image to obtain a resultant digitized resultant image.

Computer 30 is suitably programmed to recognize a discernable residual image (associated with the char smudge 37) remaining following the image subtractor stage 22, and produces an output signal directing said controlled turnstile to refuse (or block) bearer passage when a char smudge is present on said card 2, and permit passage when no char smudge is detected. The computer 30 also controls conveying mechanisms 3 and directs them to move the card 2 to the return 5a, or restrain card 2.

Further, the computer 30 is adapted to analyze the digitized resultant image of said char smudge. The presence of such a smudge, following the rapid heating phase signals the presence of explosive trace evidence. If the char smudge is in a form of at least a partial fingerprint image imparted to card 2 during said energetic reaction, the evidence will be even more significant as it will positively link the char smudge to an individual person who handled both said card 2 and explosive material resulting in said char smudge.

Thus, as card 2 is processed in this inventive system, the analysis from this checkpoint could, as shown at 32, dictate one of the following outcomes for the bearer of the subject card and/or for authorities as appropriate: "Fingerprint clean—fare adequate—Exit;" "Fingerprint clean—fare inadequate—return to entrance;" or "Fingerprint dirty—fare irrelevant—apprehend." For the last noted outcome, an alarm could be automatically sounded, or other suitable signal produced, to alert authorities, and the subject card 2 retained or confiscated with its thermographic (charred) fingerprint signature as evidence for aiding prosecution.

Auxiliary or ancillary sensing technologies may be utilized to enhance detection system effectiveness (for example, during treatment by heaters 12) and thus would serve in a confidence-building diagnostic role. For example, an in-situ ancillary trace vapor detector (T-wave) and or ion mobility spectrometer (IMS) shown at 11 and 13 respectively may be employed to document characteristic molecular vibrations or observance of an ultraviolet photon in conjunction with charring of the card 2.

Alternatively or additionally deployed auxiliary devices of the type discussed above can include a micro thermal analysis system, and/or microcantilever momentum measurement device. Such known systems are compatible with the present inventive system and process, and their inclusion obviously enhances success rates.

Figure 3:
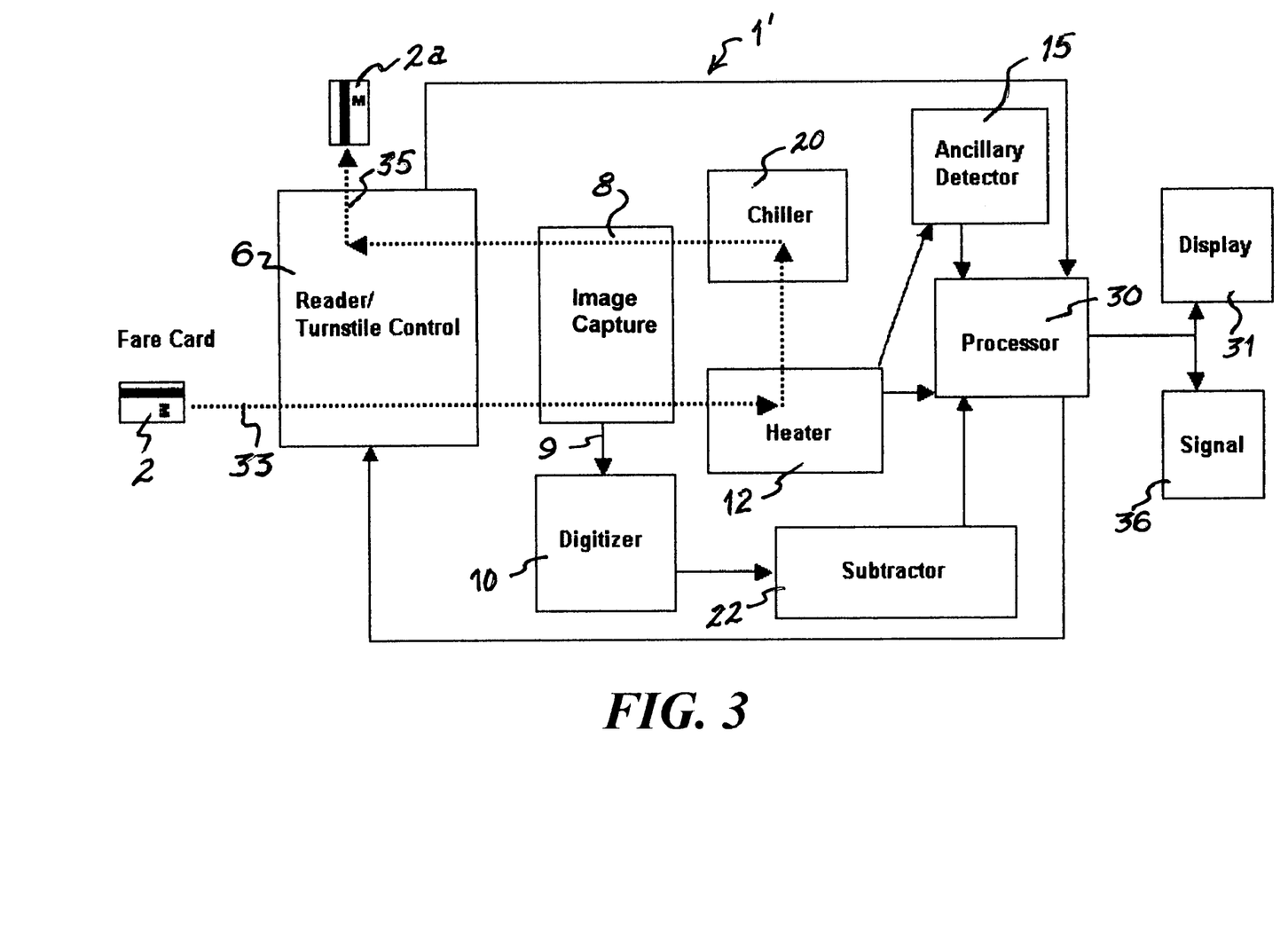
FIG. 3 is a diagrammatic illustration of the inventive system and method of detecting explosive trace evidence.

System/process diagram 1', as viewed in FIG. 3, is a simpler illustration of the present invention, and demonstrating generic application. More specifically, the system/process is presented without details of any particular controlled turnstile or gateway. Card 2 with optional coatings 2b and 2c (see FIG. 2) is fed (for example, along pathway 33) so as to be relatively presented to reader 6 and image capture stage 8 where a primary image is captured.

Digitizer 10 digitizes the captured primary image data received via conductor 9, and forwards the data to subtractor stage 22 for a purpose to be revealed below. Following initial image capture the card continues its movement relative to system 1' components where it is subjected to intense heat from heater 12. Heater 12 may comprise any of a variety of heater designs including laser, electric resistors, high temperature airflow, or the like. Such heating is immediately followed by cooling at chiller 20.

A second image capture/digitizing operation occurs following cooling at chiller 20, as the card 2 is relatively moved along pathway 34 to image capture stage 8. There, a second image of the card 2 is captured. Digitizer 10 digitizes the captured secondary image data received via conductor 9, and forwards the data to subtractor stage 22 for an automated subtraction operation. At subtractor stage 22, the digitized primary image data is subtracted from the digitized secondary image data (along with a captured image of any present char deposit). As described with respect to FIG. 1, the outcome from the subtractor stage 22, when traces of explosive are present, is the revealing of a char smudge brought on by said intense heat.

As the card 2 moves relatively to the system, and along pathway 34 and 35 to card/pass exit, the subtractor stage 22 passes its findings on to processor 30 for analysis. If a char smudge (not shown in this view) is present, as interpreted by the processor 30, information is fed to display 31 and/or a signal 36 is activated, dictating action as may be appropriate (for example, turnstile control 6 may be signaled to block the bearer. If no char smudge is present on the card 2, as shown at 2a, no adverse action is undertaken by the novel system and method described herein. In other words, in the case of a turnstile gateway, the card-holding passenger may pass freely therethrough.

Ancillary or auxiliary detector 15 is provided to enhance success rate of this system. Detector 15 may be selected from a group of trace vapor detector devices consisting of ion mobility spectrometer, micro thermal analyzer, microcantilever momentum measurement unit, T-wave, and a combination of two or more of said devices. For example, an IMS and/or a T-wave trace vapor detector unit will work in the heated environment to pick up additional evidence of the presence of explosive traces.

The term "relative" as ascribed hereabove with respect to the position of a card and various components of the inventive system is, of course, intentional and significant. For example, the claimed invention may manifest itself in an arrangement wherein a card to be "read" remains substantially stationary while addressed by a series of system components such as reader, scanner, heater, chiller and so on. While a stationary card/pass system is not illustrated, the scope of claims is intended to cover such equivalents.

Figure 4:
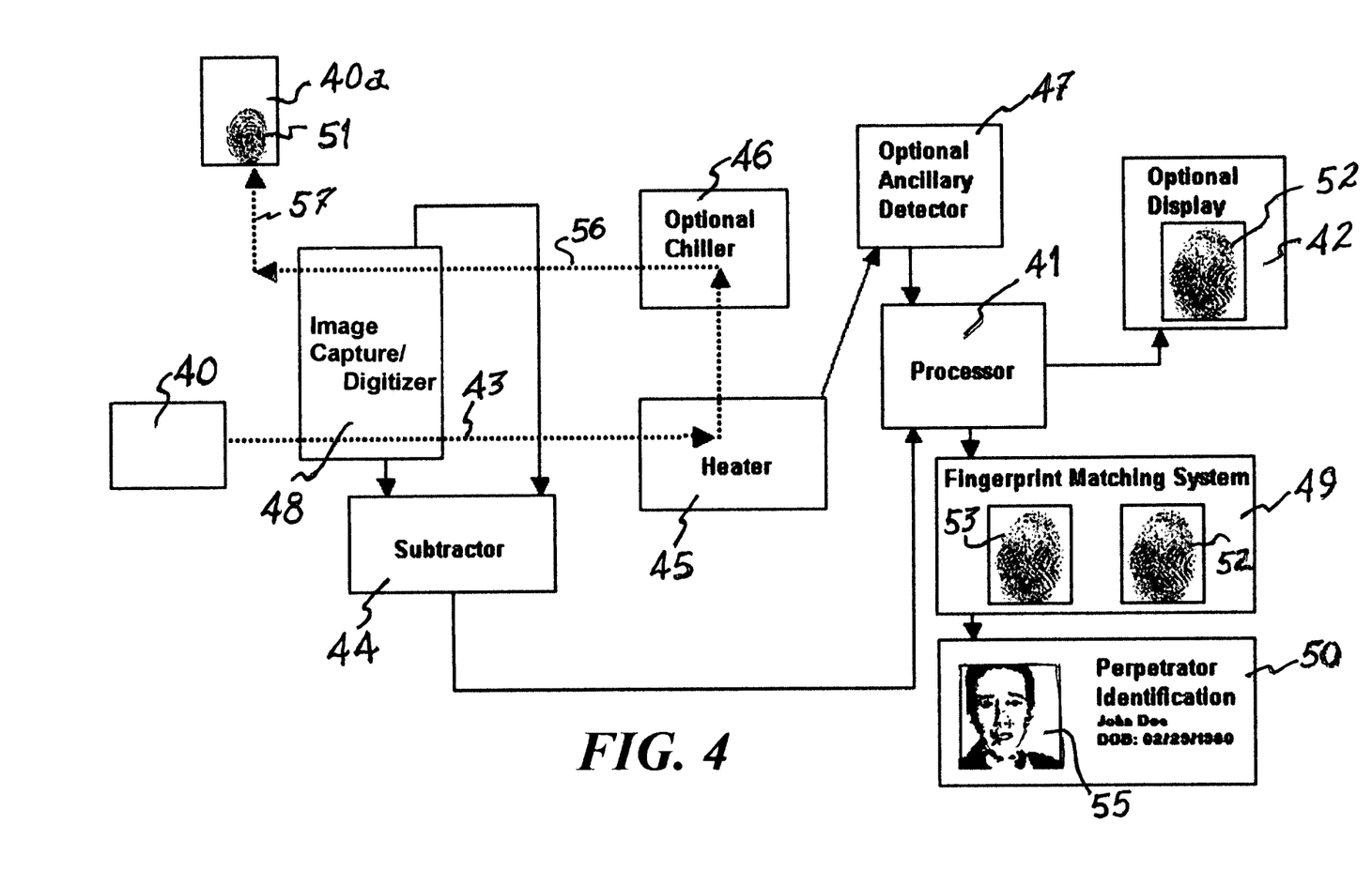
FIG. 4 is a diagrammatic illustration of another embodiment of the present inventive system and method.

FIG. 4 illustrates still another diagrammatic view of the above-described system and method, again in a generic setting. In this embodiment, the card is generically termed a medium or "substrate." This substrate or medium of interest is designated herein as 40. Substrate 40 may take any of a variety of forms including a Metrocard®, fare card, identification/key cards, passport, airline boarding passes and the like.

The substrate 40 is relatively presented (for example along a pathway 43) so as to be subjected to a first image capture stage or step by image capture/digitizer 48. Again, terms "relative" and "relatively" convey (a) an optional construct wherein a substrate is moved (as shown) or (b) an equivalent scenario wherein a substrate is inserted and remains substantially fixed (not shown) and is addressed in series by various units. At said first image capture stage or step, said image capture/digitizer 48 forms a primary digitized image of said substrate 40 transmitted to subtractor stage 44.

Departing (relatively) the image capture/digitizer 48, substrate 40 is next subjected to intense heat in a rapid heating stage or step imposed by heater 45. Rapid heating of the substrate brings the surface temperature to a level resulting in the evaporation of material deposits thereon, such as body oils, perspiration, lotions, pollen, colognes, grease, lipstick and the like.

Subsequently, as the temperature rises, explosive trace material or substance that is present will undergo an exothermic event. The result of this event is the deposition of a signature in the form of a char smudge. Since explosive trace material is generally embedded in, or adhered to, the fingertips, the signature is likely to take the form of at least a partial fingerprint as seen at 51. Substrate 40 is optionally cooled by chiller 46, and relatively presented (for example along a pathway 56) to a second image capture/digitizing stage at 48 where a secondary digitized image of said substrate 40 is captured or formulated.

Optional, auxiliary or ancillary detectors 47 may be deployed relative to said substrate 40, for example adjacent to a stage where said heating step takes place. Said detectors 47 are selected from the group of trace vapor detector devices consisting of ion mobility spectrometer, micro thermal analyzer, microcantilever momentum measurement unit, T-wave, and a combination of two or more of said devices. Use of such ancillary detector increases the confidence level for finding and identifying explosive trace evidence. In fact, there can be advantages to controlling the heat rate as applied in the heating stage by heater 45.

For example, an IMS and/or a T-wave trace vapor detector unit will operate effectively in the heated environment to pick up additional diagnostic evidence of the presence of explosive traces. Since threshold temperatures where different explosive trace materials will achieve an energetic reaction vary as much as 100 C, controlled heat application rate and careful measurement will enhance the discovery and identification of specific explosive composition. Outputs from said optional ancillary detectors are fed to processor 41.

Similar to the embodiments of FIGS. 1 and 3, digitized image signals are transmitted from image capture/digitizer 48 to subtractor stage 44 where the primary digitized image data are subtracted from the secondary digitized image data (which may include char smudge trace evidence).

An outcome or output from the subtractor stage 44, when traces of explosive are present, is the revealing of char smudge 51 brought on or deposited during said intense heat. This outcome from subtractor 44 is relayed to processor 41 (which is in the form of a programmed computer) which may display the char smudge 51 as image 52 on optional display 42. Said display 42 may also include physical identification of explosive based on data received from ancillary detectors 47 and other comparison data held in processor 41 memory.

As an added feature, FIG. 4 further illustrates the passage of information from processor 41 to fingerprint matching system (FMS) 49. In said FMS 49, the char smudge fingerprint image 52 is automatically compared against pre-identified (or known) print files to retrieve matching image 53, identified as perpetrator 55 John Doe. As in other embodiments, additional output signals from said processor 41 can dictate an array of actions, such as blocking exits, sounding a warning or silently alerting authorities.

Thus is illustrated and described a system and method for detecting an explosive using its own exothermic reaction, and in situ where it has been deposited by a perpetrator. More particularly, the inventive system and method rely upon heat energy liberated to produce an identifiable char, for example in the form of a finger print (or hand print) signature upon the surface of a substrate (e.g., Metrocard®, I.D. card, fare card, keycard, ticket, passport, boarding pass, and the like). This invention employs a differential in heating rates/energy outputs between the substrate material and explosive residue to showcase the latent fingerprints or fingerprint characteristics.

The present invention not only detects the presence of trace evidence on a substrate, but also can be refined so as to distinguish between individual explosive compositions. Threshold temperatures where different explosive materials achieve an energetic reaction may vary as much as 100 C. Thus, controlled rate of heat application and careful measurement of the temperature where energetic reaction takes place provide added diagnostics to help identify specific compositions. Identification of specific compositions will be further enhanced through the use of one or more ancillary detectors strategically operating in the area of said heater and effectively activated, for example during the rapidly heating process.

Further, the present method and system disclose the use of image processing as a complement to enhance the latent explosive signature and to identify the holder of the subject card. Additionally presented is the use of thermographic or charred fingerprint images as forensic evidence, clearly linking a perpetrator to explosive trace. Described is a unique combination of heating plate technology and chiller, coupled with before-and-after digital images, utilizing a digital subtraction technique for exposing or revealing a trace signature. This technique is performed in real time, and with minimum inconvenience or disruption of queued holders of cards, tickets or passes.

In summary, the inventive system and method are utilized as follows. A card (which term is meant to include passes, key cards, passports, tickets, I.D. cards and the like) is introduced by a card bearer at a controlled turnstile, gateway or other automatic reader facility for validation. The card is addressed by a image capture/digitizer capturing a first or primary card image and converting the image into primary image data.

Following image capture and image digitization, the card itself is subjected to rapid heating by at least one heater unit, such that at least one side of said card is subjected to intense heat to a level that causes any present trace explosive particulate to experience or exhibit an energetic reaction. Said energetic reaction is insufficient in intensity to cause damage to said card, yet sufficient to deposit a char smudge residue thereon.

The char smudge residue results from said trace explosive transferred to the card by the card holder's fingers or hands bearing trace explosive particulate. Transfers of the trace explosive and the subsequent residue deposit likely carry a pattern of at least a portion of fingerprint (or handprint) ridges, revealing identifiable whorls, loops or arches, or other definitive characteristics linkable to said card holder (the perpetrator).

After heating of the card, the card is then optionally chilled (as necessary) by at least one chiller unit and subsequently subjected to a second image capture/digitization producing a secondary (post-heated) digitized image of said card.

Both said primary and secondary image data are subjected to processing in an image subtractor stage where said primary digitized image is electronically subtracted from said secondary digitized image for the purpose of obtaining a digitized resultant image which, if present, will include the digitized image of said char smudge of said fingerprint or handprint pattern.

Next, the resultant image is automatically communicated to a computer processor adapted to receive and analyze said digitized resultant image to discern or determine the presence of said char smudge finger/hand print on said card. On discovery of said print, said computer processor can generate a display image and/or subject said char smudge to an automated fingerprint matching system (FMS) to identify the perpetrator.

An output signal from said processor can dictate any of a number of actions, from sounding a warning, refusing validation, closing a turnstile, alerting authorities and so on. Of course, the absence of an incriminating char smudge results in no adverse action being taken.

Thus, any substrate or medium presented by a bearer for validation (e.g., for passage through a turnstile, gateway or other security check point) is automatically examined; the presence of any trace explosive is detected as evidenced by char smudge resulting from said rapid heating. The system automatically refuses the bearer's validation or passage, restrains the bearer, and acts quickly to confiscate the substrate with its telltale forensic evidence to be later matched to the bearer.

Confidence in the system is increased through the use of one or more ancillary detectors strategically operating in the area of said heater and effectively activated during the rapidly heating process. The apparatus and method are enhanced by pre-coating cards or other substrates to be presented to the automatic reader, as discussed above.

Although various embodiments have been described in the foregoing detailed description and illustrated in the accompanying drawings, it will be understood that the invention is not limited to the embodiments disclosed, but may assume numerous arrangements, rearrangements, modifications, and substitutions of steps without departing from the spirit of the invention.

I claim:

1. A system for processing a card in the form of a fare card, keycard, airline boarding pass, I.D. card, passport and the like, said system positioned at a control point to determine passage or refusal of a card holder;
   said system including an automatic reader adapted to receive said card from a bearer, said reader including card intake and return, and further including a feeder mechanism defining a relative path of movement for said card from said intake to said return;
   a first image capture stage, located along said path generally adjacent said card reader, adapted to capture a first image of said card in the form of primary image data;
   a digitizer stage interconnected with said first image capture stage and adapted to receive said primary image data therefrom and to formulate a primary digitized image of said card;
   a heater unit positioned generally adjacent said first image capture stage along said path, and adapted to heat said card to a relatively high temperature such that any explosive trace substance present on said card will undergo an energetic reaction imparting a char smudge signature to said card;
   said card conveying mechanism adapted to move said card relatively with respect to said heater unit to a second image capture stage for capturing a secondary image of said card and char smudge signature in the form of secondary image data;
   said digitizer stage interconnected with said second image capture stage and adapted to receive said secondary image data therefrom and to formulate a secondary digitized image of said card;
   an image subtractor stage interconnected with said digitizer stage and adapted to receive said primary and secondary digitized images from said digitizer unit;
   said image subtractor stage further adapted to subtract said primary digitized image of said card from said secondary digitized image to obtain a digitized resultant image;
   a computer processor unit interconnected to said image subtractor stage and adapted to receive and analyze said digitized resultant image to determine the presence of a char smudge;
   said computer processor unit further adapted to transmit an output signal to said control point directing restraint of said card and bearer when char smudge signature is detected as present on said card, and directing passage permission when no char smudge is detected;
   whereby fare cards and the like presented for passage through a control point turnstile or gateway are automatically examined, the presence of any trace explosive substance is detected, and the card and card holder are permitted passage or restrained.

2. The system of claim 1 further characterized by:
   said computer processor output signal controls said card conveying mechanism to selectively move said card to the return port or to restrain further movement of said card;
   whereby cards without char smudge signature are returned and the card holder is permitted passage, while detected char smudge signature results in passage refusal for the card holder and retention of said as evidence.

3. The system of claim 2, further characterized by:
   a chiller unit positioned along said path and generally adjacent said heater unit adapted to reduce said relatively high temperature prior to movement of said card from said heater unit to said second image capture stage.

4. The system of claim 1, further characterized by:
   said first image capture stage and said second image capture stage are within a single image capture unit.

5. The system of claim 1, further characterized by:
   said computer processor unit further adapted to analyze said digitized resultant image to determine the presence of char smudge signature in the form of at least partial fingerprint image imparted to said card during said energetic reaction;
   whereby said smudge char signature can be positively linked to a person who handled both said card and said explosive.

6. The system of claim 5, wherein said computer processor is further adapted to
   compare said partial fingerprint image to a collection of pre-identified fingerprints or fingerprint characteristics in a fingerprint matching system;
   whereby said system can positively identify said bearer as perpetrator.

7. The system of claim 1, further characterized by:
   at least one ancillary detector disposed along said path;
   said at least one ancillary detector being a trace vapor detector selected from a group consisting of ion mobility spectrometer, micro thermal analyzer, microcantilever momentum measurement unit, T-wave device, and a combination of two or more of said devices;
   whereby additional diagnostic data can be collected relative to said explosive trace substance.

8. In a substrate reading system for processing a fare card, I.D. card, key card, airline boarding pass, passport and the like presented by a substrate bearer at a checkpoint for validation, said system including an automatic reader with substrate intake and return ports, and a substrate conveying mechanism defining a path of movement for said substrate from said intake port to said return port, the improvement comprising:
   an image capture/digitizer unit positioned along said path of movement generally adjacent said automatic reader and adapted to formulate a primary digitized image of said substrate;
   a rapid heating stage positioned along said path generally adjacent said image capture/digitizer unit and adapted to heat said substrate at least to a temperature level to cause explosive trace substance present on said substrate to achieve an energetic reaction imparting a char smudge signature to said substrate, yet without damaging said card;
   said substrate conveying mechanism adapted to move said substrate from said rapid heating stage to said image capture/digitizer unit for formulating a secondary digitized image of said substrate and said char smudge signature;

an image subtractor stage interconnected with said image capture/digitizer unit and adapted to receive said primary and secondary digitized images from said image capture/digitizer unit;

said image subtractor stage further adapted to subtract said primary digitized image of said substrate from said secondary digitized image to obtain a digitized resultant image;

a computer processor unit interconnected to said image subtractor stage and adapted to receive and analyze said digitized resultant image to determine presence or absence of said char smudge signature;

said processor unit further adapted to produce an output signal prompted by presence or absence of said char smudge signature;

whereby said substrate is automatically examined at said checkpoint, the presence of any trace explosive signature thereon is detected, an automatic validation decision is reached relative to the presence of said signature, and an output signal controls passage of said substrate bearer.

9. The system of claim 8, further characterized by;

a chiller unit positioned along said path and generally adjacent said heating stage adapted to rapidly cool said substrate;

said conveying mechanism adapted to move said substrate from said chiller unit to said image capture/digitizer;

whereby said substrate is rapidly cooled following said heating stage so as to avoid damage to said substrate.

10. The system of claim 8, wherein said checkpoint is a gateway;

said output signal from said processor controls said conveying mechanism to selectively move said substrate to said return port or restrain said substrate;

whereby substrates presented for passage through a gateway are automatically examined, the presence of any trace explosive substance detected, and the substrate and substrate bearer are permitted passage or restrained.

11. The card reading system of claim 10, further characterized by:

said computer processor unit being adapted to analyze said digitized resultant image to determine the presence of char smudge signature in the form of at least partial fingerprint image imparted to said substrate during said energetic reaction;

whereby said smudge char signature can be positively linked to a person who handled both said card and said explosive.

12. The system of claim 11, wherein said computer processor unit is interconnected with a fingerprint matching system;

said matching system is adapted to compare said at least partial fingerprint image to a data base collection of pre-identified fingerprints whereby said system can positively identify said presenter as perpetrator.

13. The system of claim 11, further characterized by:

at least one ancillary detector unit positioned adjacent said heating stage;

said ancillary detector adapted to identify the presence of trace explosives;

said at least one ancillary detector being a trace vapor detector selected from a group consisting of ion mobility spectrometer, micro thermal analyzer, microcantilever momentum measurement unit, T-wave device, and a combination of two or more of said devices;

whereby said ancillary detector collects and supplies additional explosive detection data to said processor for identifying said trace explosives as evidence.

14. A method of processing a substrate such as a fare card, key card, I.D. card, airline boarding pass, passport and the like so as to discern the presence thereon of trace explosive substance for determining passage or refusal of a substrate bearer through a controlled gateway, said method including the steps of:

introducing said substrate to an automatic reader for validation;

subsequently capturing a first image of said substrate;

digitizing said first image to formulate a primary digitized image of said substrate;

rapidly heating said substrate causing any present trace explosive particles to achieve an energetic reaction forming a char smudge signature on at least a portion of said substrate;

capturing a second image of said substrate following said rapid heating;

digitizing said second image to formulate a secondary digitized image of the substrate;

electronically subtracting said primary digitized image of said substrate from said secondary digitized image of said substrate and obtaining a digitized resultant image;

processing said digitized resultant image to discern presence of said char smudge signature;

automatically transmitting an output signal to said controlled gateway directing refusal of gateway passage when char smudge signature is discerned as present and to permit passage when char smudge signature is not discerned as present;

whereby a substrate in the form of a subway fare card, entry key card, airline boarding pass, passport and the like presented by its bearer for validation and gateway passage is automatically examined, the presence of any char evidence of trace explosive substance is detected, and the bearer is permitted passage or restrained.

15. The substrate processing method of claim 14, further characterized by:

automatically seizing said substrate upon said output signal when char smudge signature is present.

16. The substrate processing method of claim 14, further characterized by:

rapidly chilling the substrate following said rapidly heating step and prior to capturing said second image of said substrate.

17. The substrate processing method of claim 14, further characterized by:

processing said digitized resultant image to discern the presence of char smudge signature in the form of at least a partial fingerprint image imparted to said substrate during said energetic reaction;

positively linking said partial fingerprint image to fingerprint characteristics of said bearer who handled both said card and said explosive substance.

18. The substrate processing method of claim 14, further characterized by:

further detecting trace explosive material by applying ancillary detectors during said heating step.

19. The substrate processing method of claim 14, further characterized by:

pre-coating said substrate to be introduced to said automatic reader, said coating being in the form of a thin metallic layer;

whereby said substrate will be protected from ignition during said rapidly heating step.

20. The substrate processing method of claim 14, further characterized by:

enhancing surface adsorption characteristics of said substrate by a step of pre-coating said substrate to be introduced to said automatic reader;

said pre-coating including the application of a monolayer coating of 4-mercaptobenzoic acid;

whereby said coating will cause an increased adherence of trace explosive material to said substrate when handled by a bearer who also has handled explosive material.

21. The substrate processing method of claim 14, further characterized by:

automatically producing an alarm when char smudge signature is discerned as present thereby alerting authorities to apprehend the substrate bearer when trace explosive is detected.

* * * * *